(12) United States Patent
Corbett et al.

(10) Patent No.: US 9,918,543 B2
(45) Date of Patent: Mar. 20, 2018

(54) TOOTHBRUSH WITH CURVED NECK

(71) Applicant: Dr. Fresh, LLC, Buena Park, CA (US)

(72) Inventors: Doug Corbett, New Canaan, CT (US); Geoff Carroll, Los Angeles, CA (US); Huy Kha Nguyen, Anaheim, CA (US)

(73) Assignee: DR. FRESH, LLC, Buena Park, CA (US)

( * ) Notice: Subject to any disclaimer, the term of this patent is extended or adjusted under 35 U.S.C. 154(b) by 0 days.

(21) Appl. No.: 14/683,049

(22) Filed: Apr. 9, 2015

(65) Prior Publication Data

US 2015/0289639 A1 Oct. 15, 2015

Related U.S. Application Data

(60) Provisional application No. 61/978,079, filed on Apr. 10, 2014.

(51) Int. Cl.
  *A46B 9/04* (2006.01)
  *A46B 5/02* (2006.01)
  *A61C 17/22* (2006.01)
  *A61C 17/34* (2006.01)

(52) U.S. Cl.
  CPC ............. *A46B 9/04* (2013.01); *A61C 17/222* (2013.01); *A46B 5/028* (2013.01); *A61C 17/221* (2013.01); *A61C 17/3481* (2013.01)

(58) Field of Classification Search
  CPC ................................. A46B 9/04; A61C 17/222

USPC ........................................................ 15/167.1
See application file for complete search history.

(56) References Cited

U.S. PATENT DOCUMENTS

| 2,114,947 | A | * | 4/1938 | Warsaw | A46B 9/04 |
| | | | | | 15/167.1 |
| 4,667,360 | A | * | 5/1987 | Marthaler | A46B 5/02 |
| | | | | | 15/167.1 |
| 5,046,213 | A | * | 9/1991 | Curtis | A46B 9/04 |
| | | | | | 15/167.1 |
| D421,844 | S | * | 3/2000 | Stark | D4/104 |
| D446,393 | S | * | 8/2001 | Manfredi | D4/104 |
| 7,047,591 | B2 | * | 5/2006 | Hohlbein | A46B 5/02 |
| | | | | | 15/143.1 |
| 8,448,284 | B2 | * | 5/2013 | Gross | A46B 5/02 |
| | | | | | 15/143.1 |
| 2012/0324668 | A1 | * | 12/2012 | Stofko | A46B 5/0054 |
| | | | | | 15/167.1 |

FOREIGN PATENT DOCUMENTS

CA          2261355 A1 *  8/2000  ............. A46B 5/02

* cited by examiner

*Primary Examiner* — Laura C Guidotti
(74) *Attorney, Agent, or Firm* — Snell & Wilmer LLP

(57) ABSTRACT

A toothbrush including a handle portion, a head portion, a plurality of bristles coupled to the head portion, and a neck portion. The neck portion is curved such that the neck portion is angled in a direction away from an axis the handle portion extends upon and is then angled in a direction towards the axis.

17 Claims, 12 Drawing Sheets

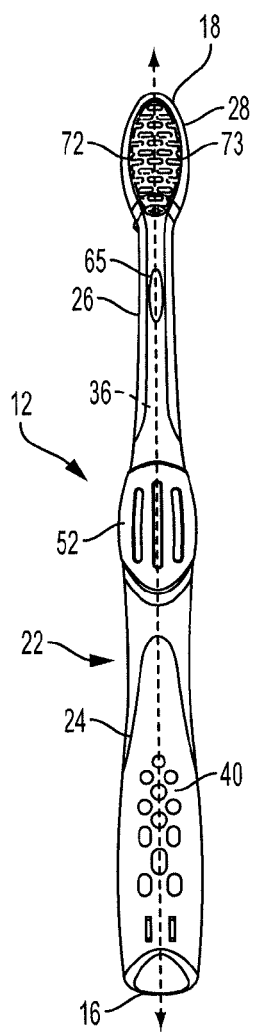
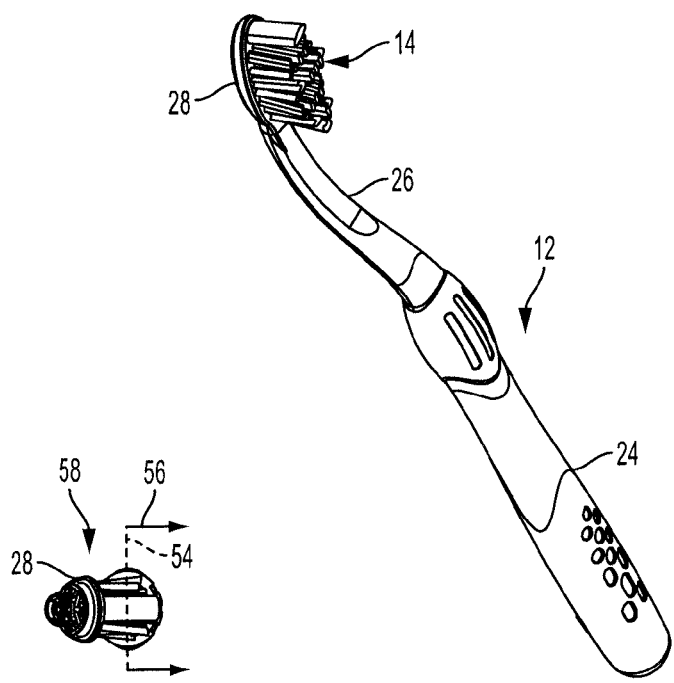
FIG. 4   FIG. 5   FIG. 6

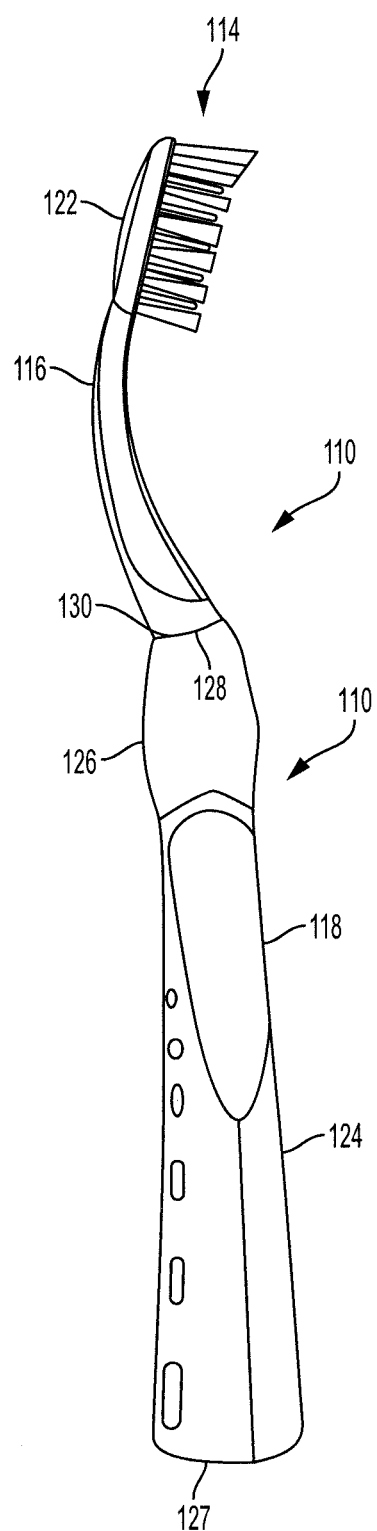
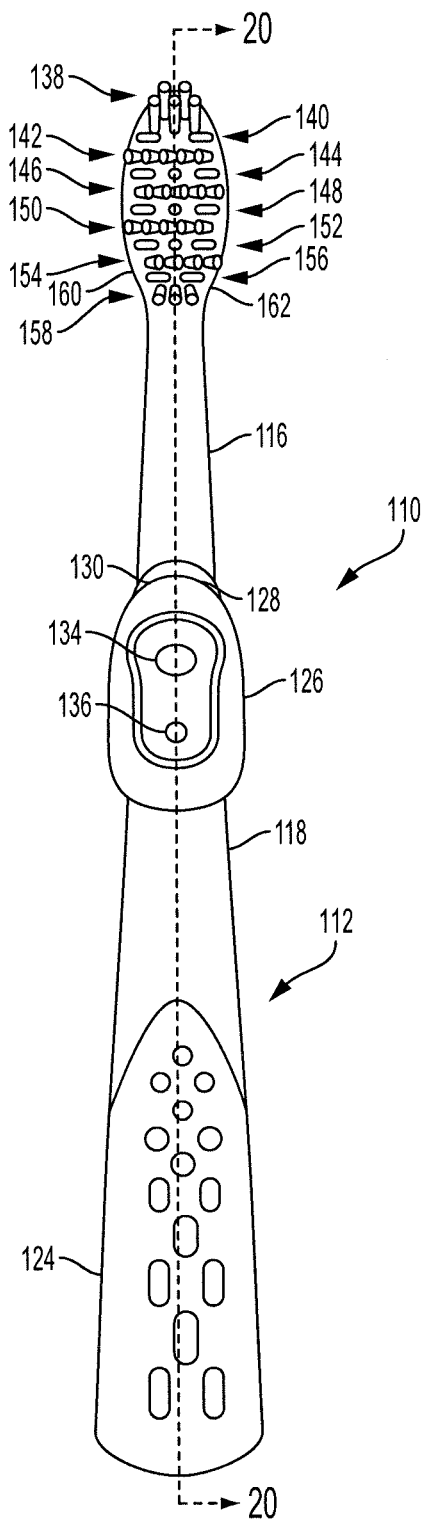
FIG. 15
FIG. 16

TOOTHBRUSH WITH CURVED NECK

CROSS REFERENCE TO RELATED APPLICATIONS

This application claims the benefit of and the priority of U.S. Provisional Application No. 61/978,079 filed on Apr. 10, 2014, the entire contents of which are herein incorporated by reference.

BACKGROUND

1. Field of the Invention

The present invention relates to dental hygiene, and more particularly to a toothbrush with a neck that is curved for better and more effective teeth cleaning.

2. Description of the Related Art

To ensure proper oral care, dentists recommend that we brush our teeth more than once a day for at least two to three minutes each time. Despite this recommendation, the average adult person does not brush his or her teeth for two to three minutes. Therefore, toothbrushes that provide better and more effective teeth cleaning can be beneficial to adults who don't have the requisite time to brush their teeth. Also, even if the proper amount of time is used to brush, a toothbrush with an improved body orientation and an improved arrangement of bristles can provide more effective teeth cleaning. Accordingly, there is a need for a toothbrush that provides advanced cleaning for more effective teeth cleaning.

SUMMARY OF THE INVENTION

According to some embodiments, a toothbrush including a handle portion, a head portion, a plurality of bristles coupled to the head portion, and a neck portion. The neck portion has a proximal end coupled to the handle portion at a juncture and a distal end coupled to the head portion. The neck portion is curved continuously from the proximal end to the distal end and is curved such that the neck portion at the proximal end is angled in a direction away from an axis the handle portion extends upon at the juncture and the neck portion at the distal end is angled in a direction towards the axis.

BRIEF DESCRIPTION OF THE DRAWINGS

The features and advantages of the embodiments of the present disclosure will become more apparent from the detailed description set forth below when taken in conjunction with the drawings. Naturally, the drawings and their associated descriptions illustrate example arrangements within the scope of the claims and do not limit the scope of the claims. Reference numbers are reused throughout the drawings to indicate correspondence between referenced elements.

FIG. 4 is a rear view of a toothbrush according to an embodiment of the disclosure.

FIG. 5 is a top view of a toothbrush according to an embodiment of the disclosure.

FIG. 6 is a left top perspective view of a toothbrush according to an embodiment of the disclosure.

FIG. 15 is a side view of a toothbrush according to an embodiment of the disclosure.

FIG. 16 is a front view of a toothbrush according to an embodiment of the disclosure.

DETAILED DESCRIPTION

In the following detailed description, numerous specific details are set forth to provide an understanding of the present disclosure. It will be apparent, however, to one of ordinarily skilled in the art that elements of the present disclosure may be practiced without some of these specific details. In other instances, well-known structures and techniques have not been shown in detail to avoid unnecessarily obscuring the present disclosure.

In the following detailed description, numerous specific details are set forth to provide an understanding of the present disclosure. It will be apparent, however, to one of ordinarily skilled in the art that elements of the present disclosure may be practiced without some of these specific details. In other instances, well-known structures and techniques have not been shown in detail to avoid unnecessarily obscuring the present disclosure.

Figure 1:
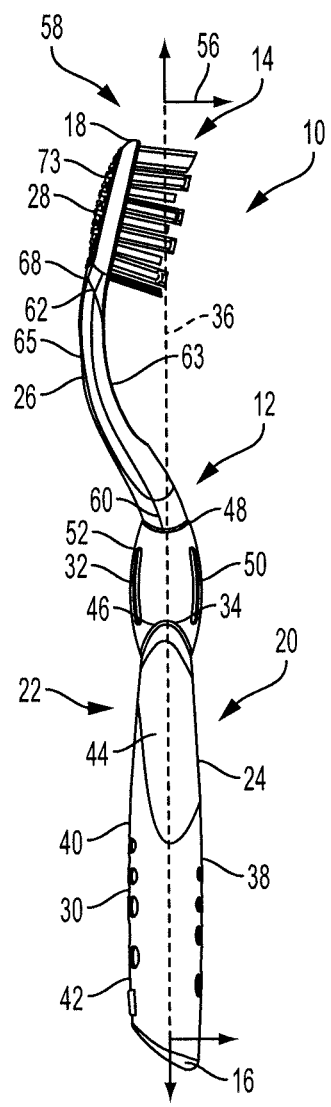
FIG. 1 is a side view of a toothbrush according to an embodiment of the disclosure.

FIG. 1 illustrates a side view of an embodiment of a toothbrush 10. The toothbrush 10 includes a body 12 and a plurality of bristles 14 extending from the body 12.

The body 12 extends from a proximal end 16 to a distal end 18 and is configured to be gripped by a user and inserted into the user's mouth to position the bristles 14 on the user's teeth. The body 12 includes a dorsal side 20, which is the front side of the toothbrush 10, and a ventral side 22, which is the back side of the toothbrush 10. The bristles 14 extend from the dorsal side 20 of the body 12.

The body 12 may include a handle portion 24, a neck portion 26, and a head portion 28. The handle portion 24 may include a base portion 30 and a grip portion or thumb grip portion 32.

The base portion 30 has a distal end 34 and a proximal end that defines the proximal end 16 of the body 12. The base portion 30 may have a longitudinal shape as shown and may extend upon an axis 36. The base portion 30 may have a dorsal surface 38 at the dorsal side 20 of the body 12, and a ventral surface 40 at the ventral side 22 of the body 12. The base portion 30 may have a triangular shape when viewed along a cross section transverse to the body 12, with two vertices of the triangular shape being on the dorsal side 20 of the body 12, and one vertex being on the ventral side 22 of the body 12. The base portion 30 may be made out of a combination of materials. For example, the base portion 30 may be made of pliant material 42 and rigid material 44. The combination of pliant and rigid material may provide a firm yet cushioned structure for the base portion 30. The pliant material 42 may extend around the base portion 30 and include openings that expose portions of the rigid material 44. The base portion 30 may be configured to be held in the palm of a user's hand during use of the toothbrush 10. In one embodiment, the base portion 30 may have a different shape or structure than shown in FIG. 1.

The base portion 30 is positioned adjacent to the thumb grip portion 32. The distal end 34 of the base portion 30 couples to a proximal end 46 of the thumb grip portion 32 at a juncture. The juncture is the point of transition between the respective ends 34, 46. The thumb grip portion 32 extends away from the proximal end 46 of the thumb grip portion 32 to a distal end 48 of the thumb grip portion 32. The distal end 48 of the thumb grip portion 32 may define the distal end of the handle portion 24. The thumb grip portion 32 may have a longitudinal shape as shown and may extend upon axis 36. The thumb grip portion 32 may have a dorsal surface 50 at the dorsal side 20 of the body 12, and a ventral surface 52 at the ventral side 22 of the body 12. The thumb grip portion 32 may have a round or oval shape when viewed along a cross section transverse to the body 12. The thumb grip portion 32 may be made out of a combination of materials. For example, the thumb grip portion 32 may be made of pliant material 54 and rigid material 57 (marked in FIG. 3). The combination of pliant and rigid material may provide a firm yet cushioned structure for the thumb grip portion 32. The pliant material may extend around the thumb grip portion 32 and include openings that expose portions of the rigid material 57. The thumb grip portion 32 may be configured to be gripped by a user's thumb during use of the toothbrush 10. In one embodiment, the thumb grip portion 32 may have a different shape or structure than shown in FIG. 1.

The base portion 30 and thumb grip portion 32 may extend upon the same axis 36. The handle portion 24 may accordingly extend upon the axis 36. The axis 36 may represent a midline of the handle portion 24, as shown in FIG. 1, or the line that equal amounts of the handle portion 24 are positioned about. The axis 36 may also extend upon a midplane 54 (marked in FIG. 5) that divides the handle portion 24 into substantially equal halves and defines the boundary between the dorsal side 20 and the ventral side 22 of the body 12 along the handle portion 24. The dorsal side 20 of the handle portion 24 may be positioned on a first side 56 of midplane 54 (marked with an arrow in FIG. 5) and the ventral side 22 may be positioned on a second side 58 (marked opposite the side with the arrow in FIG. 5) of the midplane 54. In one embodiment, the handle portion 24 may have a curved shape such that the entirety of the handle portion 24 does not extend upon a single axis. In one embodiment, the handle portion 24 may have a different shape or structure than shown in FIG. 1, yet remain configured for a user's hand to grip.

The neck portion 26 has a proximal end 60 that couples to the distal end 48 of the thumb grip portion 32 and the handle portion 24 at a juncture. The juncture is the point of transition between the respective ends 48, 60. The neck portion 26 is positioned adjacent to the thumb grip portion 32. The neck portion 26 extends away from the proximal end 60 of the neck portion 26 to the distal end 62 of the neck portion 26. The neck portion 26 may have a dorsal surface 63 at the dorsal side 20 of the body 12, and a ventral surface 65 at the ventral side 22 of the body 12. The neck portion 26 is curved, and is preferably curved continuously along its extent. The neck portion 26 may be curved such that the neck portion at the proximal end 60 is angled in a direction away from the dorsal side 20 of the body 12, and the neck portion 26 at the distal end 62 is angled towards the dorsal side 20 of the body 12. With regard to the thumb grip portion 32, the thumb grip portion 32 at the juncture with the neck portion 26 extends upon axis 36. The neck portion 26 at the proximal end 60 is angled in a direction away from the axis 36, and at the distal end 62 is angled in a direction towards the axis 36. In one embodiment, the base portion 30 may be curved such that it does not extend upon the axis that the thumb grip portion 32 extends upon at the juncture with neck portion 26, yet the neck portion 26 may angle away and towards the axis that the thumb grip portion 32 extends upon at the juncture as shown in FIG. 1. As such, the neck portion 26 may be angled with regard to the axis that the thumb grip portion 32 extends upon at the juncture, regardless of whether other portions of the grip portion 32 or base portion 30 extend upon a different axis. With regard to the midplane 54, the neck portion 26 at the proximal end 60 is angled in a direction away from the first side 56 of the plane 54 and is angled in a direction towards the first side 56 at the distal end 62 of the neck portion 26. The neck portion 26 may have a concave curvature relative to the dorsal side 20 of the body 12 and a concave curvature relative to the axis 36 and first side 56 of the plane 54. The neck portion 26 may angle away from the direction of extent of the thumb grip portion 32 at the proximal end 60 and angle in an opposite direction towards the direction of extent at the distal end 62.

Figure 2:
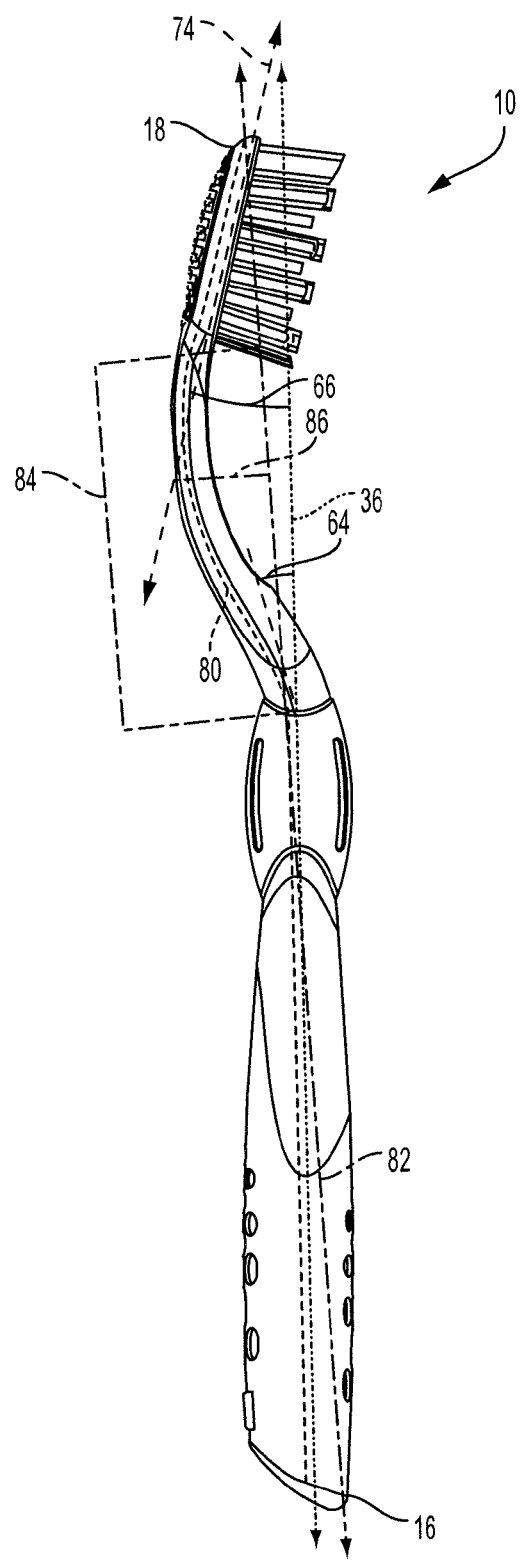
FIG. 2 is a side view of a toothbrush according to an embodiment of the disclosure.

The neck portion 26 at the proximal end 60 may have an angle 64 (marked in FIG. 2) relative to the axis 36 of between about thirteen (13) to twenty (20) degrees, and is preferably about fifteen (15) degrees. The neck portion 26 at the distal end 62 may have an angle 66 (marked in FIG. 2) relative to the axis 36 of between about eleven (11) to eighteen (18) degrees, and is preferably about fourteen (14) degrees. The neck portion 26 may be configured to extend the head portion 28 away from the neck portion 26 such that the head portion 28 may reach the teeth of the user, or may be otherwise defined as a portion of the body 12 that starts a continuous curve concave relative to the dorsal side 20 of the body 12. In one embodiment, the dimensions and angles of the neck portion may be varied.

A proximal end 68 of the head portion 28 couples to the distal end 62 of the neck portion 26 at a juncture. The juncture is the point of transition between the respective ends 62, 68. The head portion 28 is configured to couple to the plurality of bristles 14. The head portion 28 may be angled to the same extent as the distal end 62 of the neck portion 26. For example the head portion 28 may be angled at the degree of angle 66 shown or described in regard to FIG. 2. The head portion 28 may have a dorsal surface 70 (marked in FIG. 3) at the dorsal side 20 of the body 12, and a ventral surface 72 (marked in FIG. 4) at the ventral side 22 of the body 12. The dorsal surface 70 may be substantially flat and extend at the angle 66 shown or described in regard to FIG. 2. A tongue scraper 73 may be positioned on the ventral surface 72.

The neck portion 26 may be curved such that the head portion 28 does not pass through the midplane 54, and does not pass through the axis 36. The head portion 28 may be positioned entirely on the second side 58 of the midplane 54. The head portion 28 may be offset from the plane 54 and axis 36 and angled in a direction towards axis 36. The head portion 28 may extend along an axis 74 that intersects axis 36. The plurality of bristles 14 extend from head portion 28 in a direction toward axis 36 and away from the second side 58 of the midplane 54.

The neck portion 26 represents a substantial portion of the length of the body 12. With regard to a midline distance 80 (marked in FIG. 2) of the body 12, taken along a midline of the body 12, the neck portion 26 represents at least about twenty five (25) percent of the midline distance 80 of the body 12. With regard to a linear distance 82 of the body 12 from the proximal end 16 to the distal end 18, the linear distance 84 of the neck portion parallel to the linear distance 82 of the body 12 is at least about twenty five (25) percent of the linear distance of the body 12. The displacement 86 of the neck portion 26 from the linear distance 82 of the body 12 is at least about six (6) percent of the linear distance 82. In one embodiment, these dimensions may be varied.

Figure 3:
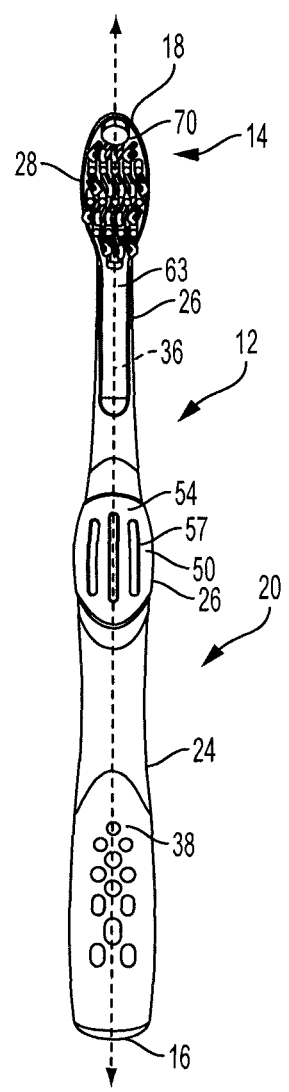
FIG. 3 is a front view of a toothbrush according to an embodiment of the disclosure.

FIG. 3 illustrates a front view of toothbrush 10. The body 12 may be substantially symmetrical about the axis 36. The neck portion 26 may have a width along the entirety of its extent that is less that the width of the thumb grip portion 32. The neck portion 26 may have a width along the entirety of its extent that is less than the width of the head portion 28.

FIG. 4 illustrates a rear view of toothbrush 10. The tongue scraper 73 may include a pattern of raised portions separated by lower portions, with the raised portions configured to scrub a user's tongue.

FIG. 5 illustrates a top view of toothbrush 10. The head portion 28 may be angled towards the first side 56 of the midplane 54, yet may not pass through the midplane 54.

Figure 8:
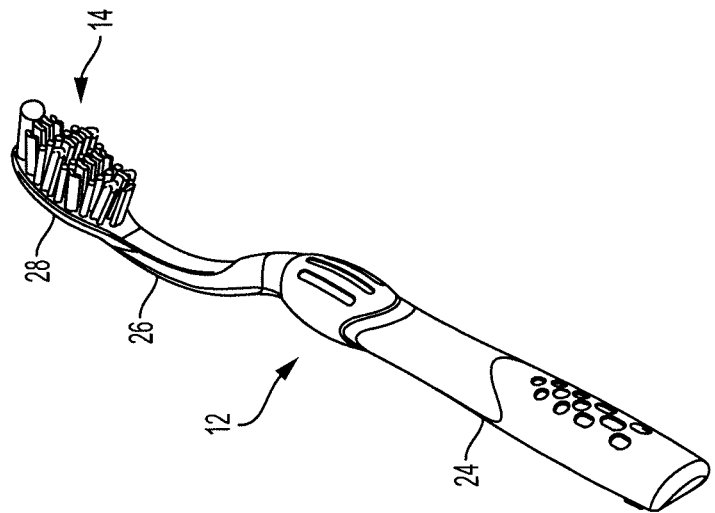
FIG. 8 is a left bottom perspective view of a toothbrush according to an embodiment of the disclosure.
Figure 7:
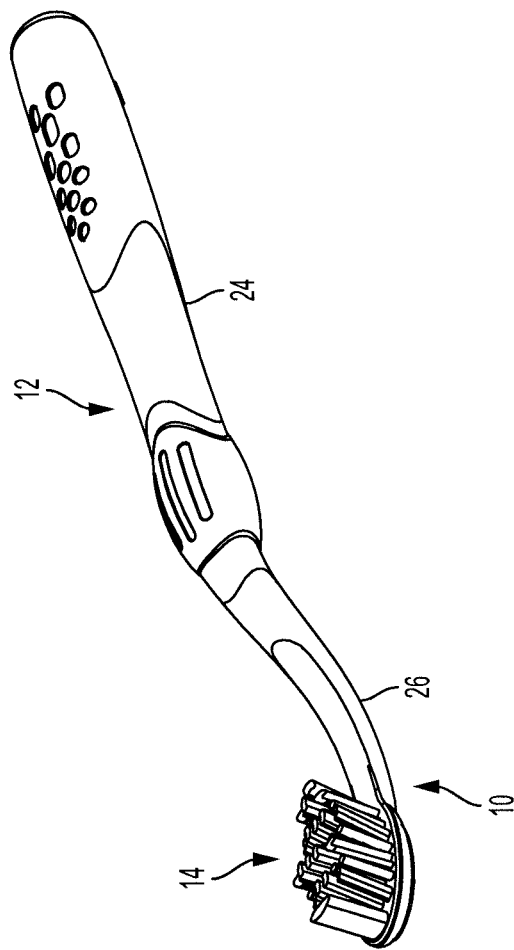
FIG. 7 is a left top perspective view of a toothbrush according to an embodiment of the disclosure.

FIGS. 6 and 7 illustrate top left perspective views of the toothbrush 10. FIG. 8 illustrates a bottom left perspective view of the toothbrush 10.

A toothbrush including features as discussed in regard to FIGS. 1-8, particularly the curved features of the neck portion, has been found to provide improved access to teeth in the rear of the user's mouth, increasing ease of use of the toothbrush. The curved neck portion allows the user to more easily insert the toothbrush into the back of the user's mouth without being blocked by other portions of the mouth. The angle of the head portion 28 has also been shown to provide an improved scrubbing angle against the teeth in the rear of the user's mouth. The scrubbing angle allows the bristles 14 to more easily clean plaque and other residue from the user's teeth when the toothbrush 10 is moved to a variety of positions in the user's mouth.

Figure 9:
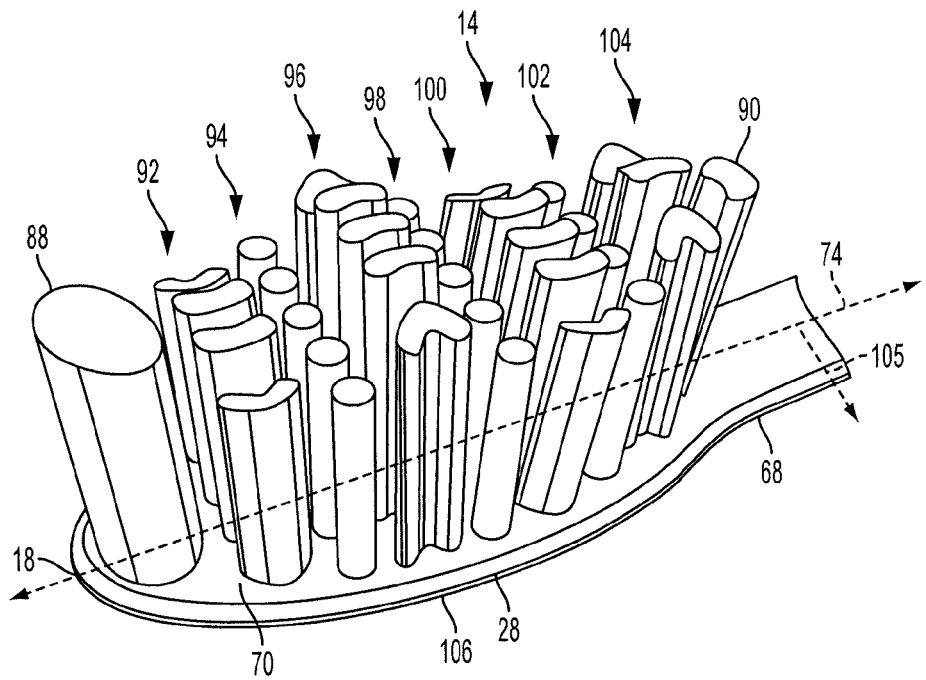
FIG. 9 is a top left perspective view of a toothbrush head according to an embodiment of the disclosure.

FIG. 9 illustrates a top left perspective view of head portion 28 showing bristles 14 extending from dorsal surface 70 of the head portion 28. The bristles 14 may be grouped into tufts. The tufts may include a toe tuft 88, a heel tuft 90, and a plurality of rows 92, 94, 96, 98, 100, 102, 104 of bristle tufts.

The toe tuft 88 may be positioned adjacent the distal end 18 of the head portion 28. The toe tuft 88 may be angled towards the distal end 18 of the head portion 28, as shown in FIG. 9. The toe tuft 88 may have a round or substantially circular footprint, which is the cross sectional appearance of the tuft from a top plan view. The toe tuft 88 may have a bristle profile, which is the appearance of the free ends of the tuft from a side plan view, that is angled upwards as the toe tuft 88 extends in a direction towards the distal end 18 of the head portion 28. The free ends of the bristles of the toe tuft 88 more proximal to the distal end 18 of the head portion 28 may be higher than the free ends of the bristles of the toe tuft 88 more proximal to the proximal end 68 of the head portion 28.

The heel tuft 90 may be positioned adjacent the proximal end 68 of the head portion 28. The heel tuft 90 may be angled towards the proximal end 68 of the head portion 28, as shown in FIG. 9. The heel tuft 90 may have a v-shape footprint that encloses an area. The heel tuft 90 may have a bristle profile that is angled upwards as the heel tuft 90 extends in a direction towards the proximal end 68 of the head portion 28. The free ends of the bristles of the heel tuft 90 more proximal to the proximal end 68 of the head portion 28 may be higher than the free ends of the bristles of the heel tuft 90 more proximal to the distal end 18 of the head portion 28.

The plurality of rows 92, 94, 96, 98, 100, 102, 104 of bristle tufts may each include tufts aligned in a direction transverse to the axis 74 that the head portion 28 extends upon. Row 92 may include tufts 92a, 92b, 92c, 92d (marked in FIG. 10) aligned in a transverse direction 105 to the axis 74. Each tuft in row 92 may be aligned towards the left side 106 of the head portion by an angle of between about four (4) and ten (10) degrees to the dorsal surface 70. Preferably, the tufts of row 92 are each angled by about seven (7) degrees to the left. The tufts of row 92 may each have a v-shape footprint that encloses an area. The tufts 92a, 92d may have a footprint that has a greater angled v-shape than the tufts 92b, 92c. The tufts 92a, 92d may have a bristle profile that angles upwards as the tufts 92a, 92d extend towards left side 106. The tufts 92b, 92c may have a bristle profile that is flat. The bristle profile of tufts 92b, 92c may extend parallel to the dorsal surface 70 of head portion 28.

Rows 94, 98, 102 may include tufts aligned in a direction transverse 105 to axis 74. Each tuft of row 94, 98, 102 may extend substantially perpendicular to the dorsal surface 70. Each tuft of row 94, 98, 102 may have a round or substantially circular footprint. Each tuft of row 94, 98, 102 may have a bristle profile that is flat, and extends parallel to the dorsal surface 70.

Row 96 may include tufts 96a, 96b, 96c, 96d, 96e (marked in FIG. 10) aligned in a transverse direction 105 to the axis 74. Each tuft in row 96 may be aligned towards the right side 108 of the head portion (marked in FIG. 11) by an angle of between about four (4) and ten (10) degrees to the dorsal surface 70. Preferably, the tufts of row 96 are each angled by about seven (7) degrees to the right. The tufts of row 96 may each have a v-shape footprint that encloses an area. The tufts 96a, 96e may have a footprint that has a greater angled v-shape than the tufts 96b, 96c, 96d. The tufts 96a, 96e may have a bristle profile that angles upwards as the tufts 96a, 96e extend towards right side 108. The tufts 96b, 96c, 96d may have a bristle profile that is flat. The bristle profile of tufts 96b, 96c, 96d may extend parallel to the dorsal surface 70 of head portion 28.

Row 100 may include tufts 100a, 100b, 100c, 100d, 100e (marked in FIG. 10) aligned in a transverse direction 105 to the axis 74. Each tuft in row 100 may be aligned towards the left side 106 of the head portion by an angle of between about four (4) and ten (10) degrees to the dorsal surface 70. Preferably, the tufts of row 100 are each angled by about seven (7) degrees to the right. The tufts of row 100 may each have a v-shape footprint that encloses an area. The tufts 100*a*, 100*e* may have a footprint that has a greater angled v-shape than the tufts 100*b*, 100*c*, 100*d*. The tufts 100*a*, 100*e* may have a bristle profile that angles upwards as the tufts 100*a*, 100*e* extend towards left side 106. The tufts 100*b*, 100*c*, 100*d* may have a bristle profile that is flat. The bristle profile of tufts 100*b*, 100*c*, 100*d* may extend parallel to the dorsal surface 70 of head portion 28.

Row 104 may include tufts 104*a*, 104*b*, 104*c* (marked in FIG. 10) aligned in a transverse direction 105 to the axis 74. Each tuft in row 104 may be aligned towards the right side 108 of the head portion by an angle of between about four (4) and ten (10) degrees to the dorsal surface 70. Preferably, the tufts of row 104 are each angled by about seven (7) degrees to the right. The tufts of row 104 may each have a v-shape footprint that encloses an area. The tufts 104*a*, 104*c* may have a footprint that has a greater angled v-shape than the tuft 104*b*. The tufts 104*a*, 104*c* may have a bristle profile that angles upwards as the tufts 104*a*, 104*c* extend towards right side 108. The tuft 104*b* may have a bristle profile that is flat. The bristle profile of tuft 104*b* may extend parallel to the dorsal surface 70 of head portion 28.

The rows 92, 94, 96, 98, 100, 102, 104 of bristle tufts extend in alternating directions, with the rows 92, 100 angled towards the left side 106 of the head portion 28, the rows 96, 104 angled towards the right side 108 of the head portion 28, and the rows 94, 98, 102 not angled to either side 106, 108. The rows 92, 96, 100, 104 may be considered to be angled relative to the direction that the tufts of rows 94, 98, 102 extend in. Alternating adjacent rows 92, 96, 100, 104 may be angled in opposite directions from each other. The alternating adjacent rows 92, 96, 100, 104 may be angled relative to the adjacent intervening rows 94, 98, 102. The bristle profiles of the tufts 92*a*, 92*d*, 96*a*, 96*e*, 100*a*, 100*e*, 104*a*, 104*c* may be considered to be angled relative to the bristle profiles of tufts 94, 98, 102 and tufts 92*b*, 92*c*, 96*b*, 96*c*, 96*d*, 100*b*, 100*c*, 100*d*, 104*b*. The upper ends of the tufts of rows 92, 96, 100, 104 may be positioned higher than the ends of tufts of rows 94, 98, 102.

Figure 10:
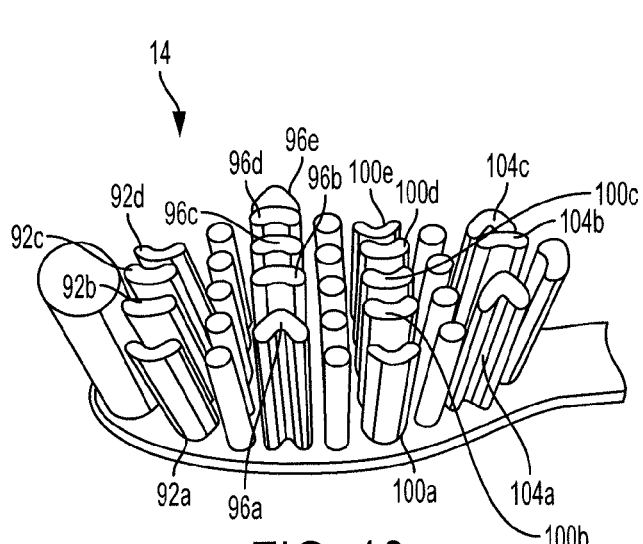
FIG. 10 is a left side perspective view of a toothbrush head according to an embodiment of the disclosure.
Figure 11:
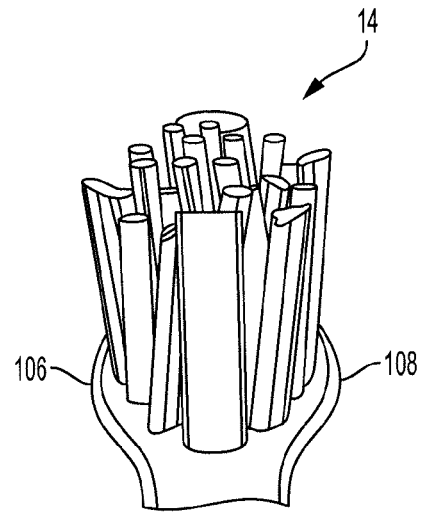
FIG. 11 is a bottom perspective view of a toothbrush head according to an embodiment of the disclosure.

FIG. 10 illustrates a side perspective view of the bristles 14. FIG. 11 illustrates an end perspective view of bristles 14. In one embodiment, the configuration of bristles 14 may be varied from the configuration that is shown in FIGS. 9-11.

The configuration of bristles 14 shown in FIGS. 9-11 have been found to have superior ability for tooth cleaning, including interdental cleaning. The angled rows of bristles may allow for scrubbing and polishing action against the teeth as the rows 92, 96, 100, 104 angled in opposing directions are swept against the teeth. The rows 92, 96, 100, 104 angled towards the direction of movement may provide a scrubbing effect at the same time the rows 92, 96, 100, 104 angled away from the direction of movement provide a polishing effect. In addition, the columnar rows 94, 98, 102 may polish the teeth as the longer angled rows 92, 96, 100, 104 extend between teeth. The configuration of bristles 14 in combination with the structure of body 12 shown in FIGS. 1-7 has been found to enhance this cleaning ability, by the improved access to teeth and cleaning angle of the head portion offered by body 12.

Figure 12:
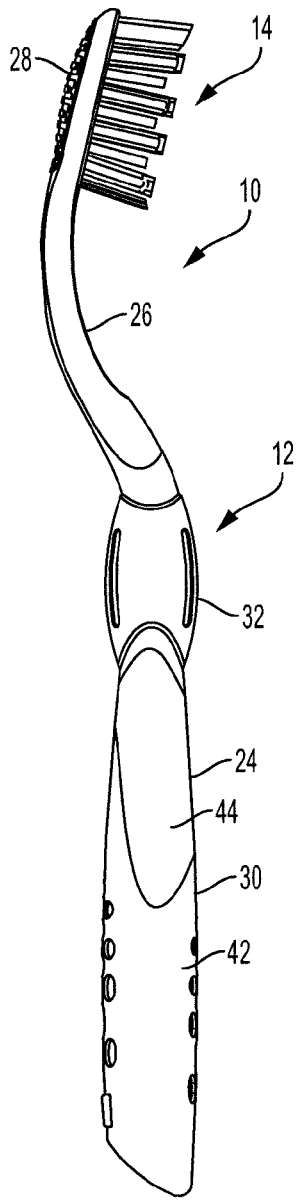
FIG. 12 is a side view of a toothbrush according to an embodiment of the disclosure.
Figure 13:
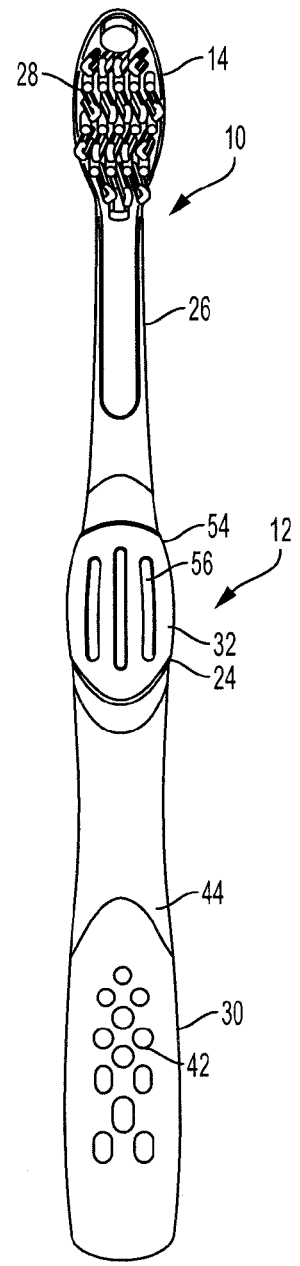
FIG. 13 is a front view of a toothbrush according to an embodiment of the disclosure.
Figure 14:
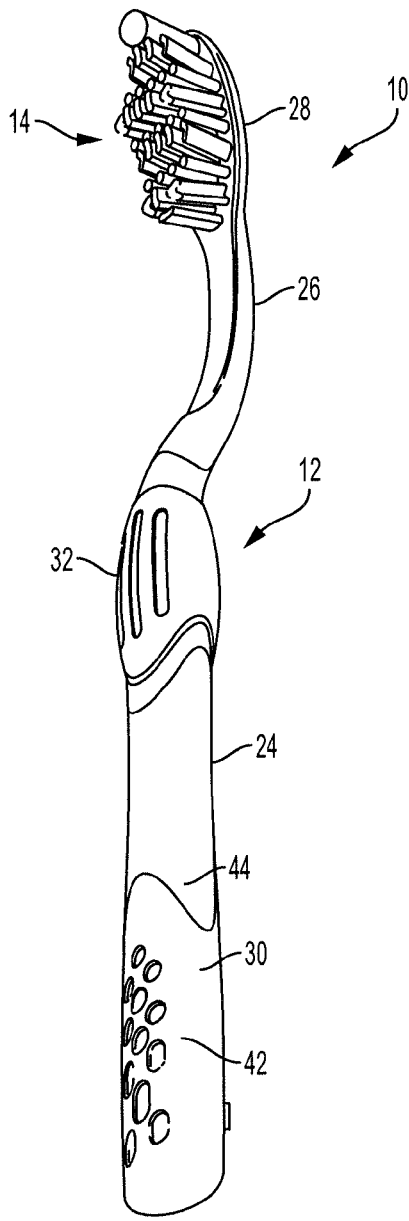
FIG. 14 is a right side perspective view of a toothbrush according to an embodiment of the disclosure.

FIG. 12 illustrates a side view of toothbrush 10. FIG. 13 illustrates a front view of toothbrush 10. FIG. 14 illustrates a front right perspective view of toothbrush 10.

In one embodiment, the body 12 may have a different shape or structure than shown in FIGS. 1-7 and 12-14.

FIG. 15 illustrates a side view of an embodiment of a toothbrush 110 including a body 112 having a neck portion 116 that is separable from the handle portion 118. The features and dimensions of the toothbrush 10 apply to the toothbrush 110 unless otherwise stated.

The body 112 may include the handle portion 118, the neck portion 116, and a head portion 122. A plurality of bristles 114 may extend form the head portion 122. The handle portion 118 may include a base portion 124 and a grip portion or thumb grip portion 126. The proximal end 127 of the handle portion 118 may be configured to be substantially flat, such that the toothbrush 110 may stand upright upon a surface.

The neck portion 116 may be configured to separate from the handle portion 118 at the distal end 128 of the handle portion and the proximal end 130 of the neck portion 116.

The toothbrush 110 may include a motor 132 (marked in FIG. 20) configured to move the bristles 114. The motor 132 may be configured to vibrate to move the bristles 114 such that they provide improved scrubbing of the user's teeth. The bristles 114 may be configured to vibrate based on the motion of the motor 132. In one embodiment, the bristles 114 may be configured to vibrate for at least 20,000 strokes per minute. In one embodiment, the bristles 114 may be configured to vibrate for at least 24,000 strokes per minute. In one embodiment, the motor 132 may be configured to rotate the bristles 114 or impart other forms of motion to the bristles 114.

FIG. 16 illustrates a front view of the toothbrush 110. The toothbrush 110 may include a power switch 134 for controlling power to the motor 132. The power switch 134 may be configured to be pressed to turn on the motor 132, and may be pressed to turn off the motor 132. In the embodiment shown in FIG. 16, an off switch 136 is included to turn off the motor 132. The off switch 136 may be utilized in an embodiment in which pressing the power switch 134 does not turn off the motor 132. The power switch 134 and off switch 136 may be positioned on the thumb grip portion 126, and may be positioned adjacent to one another.

The bristles 114 may include multiple toe tufts 138 and a series of rows 140, 142, 144, 146, 148, 150, 152, 154, 156, 158 of bristle tufts and gum massagers. Row 140 may include gum massagers. Row 158 may include bristle tufts. Rows 142, 150 may include bristle tufts angled towards the left side 160 of the head portion 122. Rows 148, 156 may include bristle tufts angled towards the right side 162 of the head portion 122. The rows 142, 150, 148, 156 may alternate in angle direction. Each tuft in rows 142, 150, 148, 156 may be at an angle of between about four (4) and ten (10) degrees, preferably, the tufts of rows 142, 150, 148, 156 may be each angled by about seven (7) degrees. Rows 144, 148, 152, 156 may include both gum massagers and bristle tufts. The gum massagers and bristle tufts of rows 140, 144, 148, 152, 156, 158 may extend substantially upwards from the head portion 122.

In one embodiment, the bristles 114 may be configured as the bristles 14 shown in FIGS. 9-11. In one embodiment, the bristles 114 may have an alternative configuration. In one embodiment, the bristles 14 may be configured as the bristles 114 shown in FIG. 16.

Figure 17:
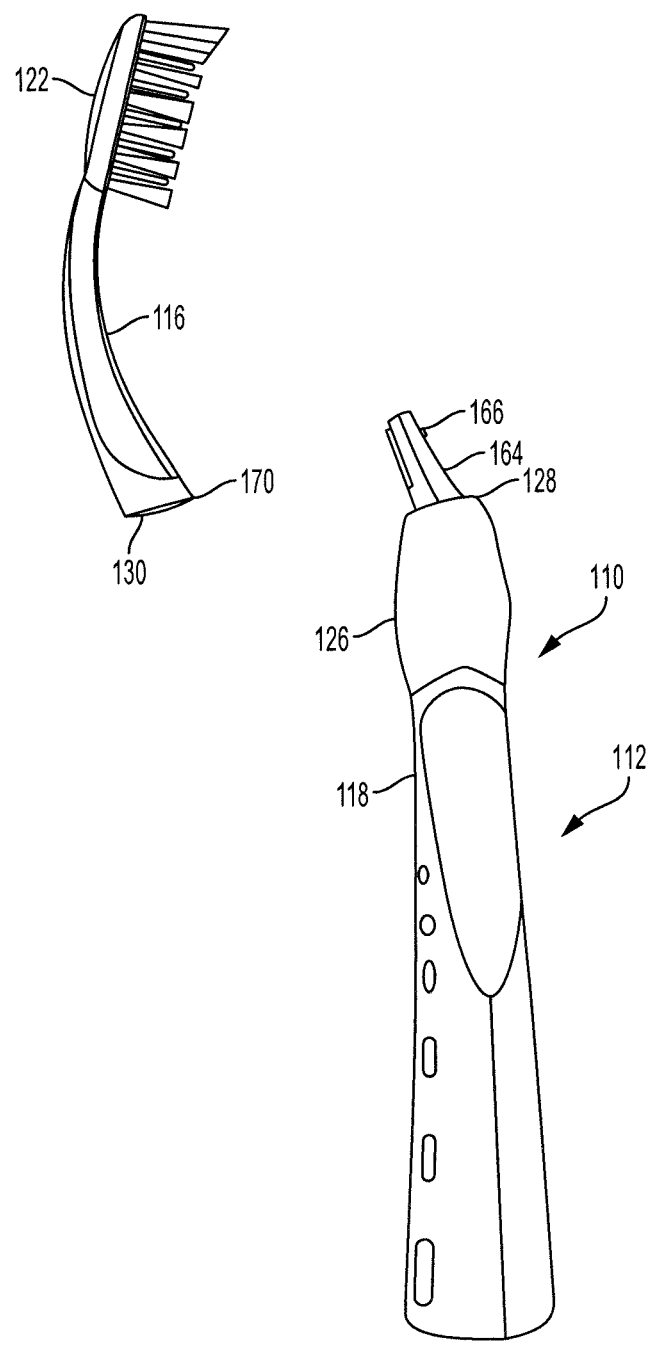
FIG. 17 is a side view of a toothbrush according to an embodiment of the disclosure with neck portion separated from a handle portion.

FIG. 17 illustrates a side view of the toothbrush 110 with the neck portion 116 separated from the handle portion 118. The handle portion 118 may include a connector device 164 positioned at the distal end 128 of the handle portion 118. The connector device 164 may form a protrusion in the form of a post that is positioned at the distal end 128. The connector device 164 may be angled towards the ventral side of the body 112. The connector device 164 may include a catch 166. The catch 166 may be positioned on a dorsal surface of the connector device 164. The catch 166 may be in the form of a ridge on the dorsal surface.

The neck portion 116 may be configured to separably couple to the handle portion 118 via the connector device 164. The connector device 164 may be configured to insert into the neck portion 116 to separably couple to the neck portion 116. The neck portion 116 may include a cavity 168 (marked in FIG. 20) that receives the connector device 164. The connector device 164 may insert into the cavity 168 to separably couple to the neck portion 116, and may be slid out of the cavity 168 to separate from the neck portion 116. The proximal end 130 of the neck portion 116 may include pliant material 170 in the form of a skirt. The pliant material 170 may extend over the distal end 128 of the handle portion 118 and may form a water seal of the coupling between the neck portion 116 and the handle portion 118.

Figure 18:
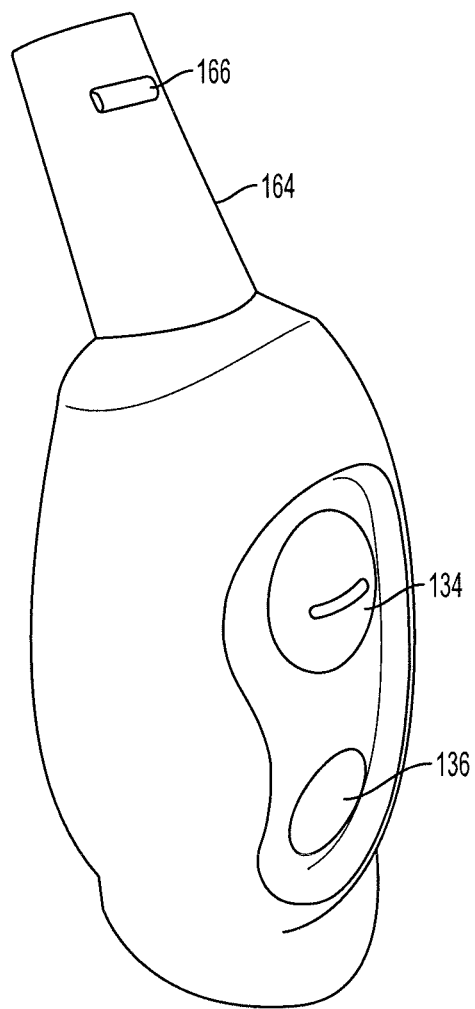
FIG. 18 is a close-up view of a dorsal surface of a connector device according to an embodiment of the disclosure.
Figure 19:
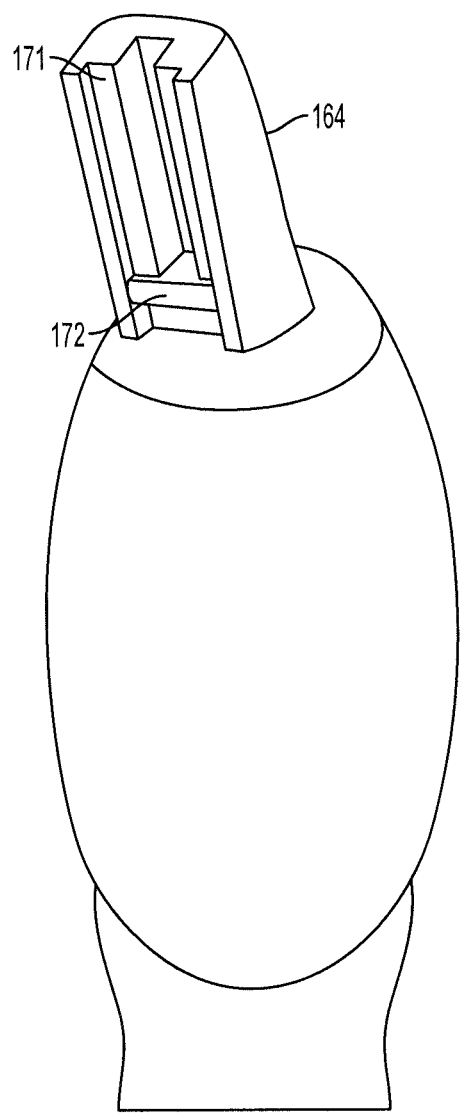
FIG. 19 is a close-up view of a ventral surface of a connector device according to an embodiment of the disclosure.

FIG. 18 illustrates a close-up view of the dorsal surface of the connector device 164. FIG. 19 illustrates a close-up view of the ventral surface of the connector device 164. The ventral surface may include a track 171 in the form of a recess for receiving a mating track of the neck portion 116. The track 171 may slide along the mating track to align the neck portion 116 and the handle portion 118 when the connector device 164 is inserted into the neck portion 116. The ventral surface of the connector device 164 may include a catch 172 in the form of a ridge on the ventral surface. The catch 172 may be positioned along the track 171.

Figure 20:
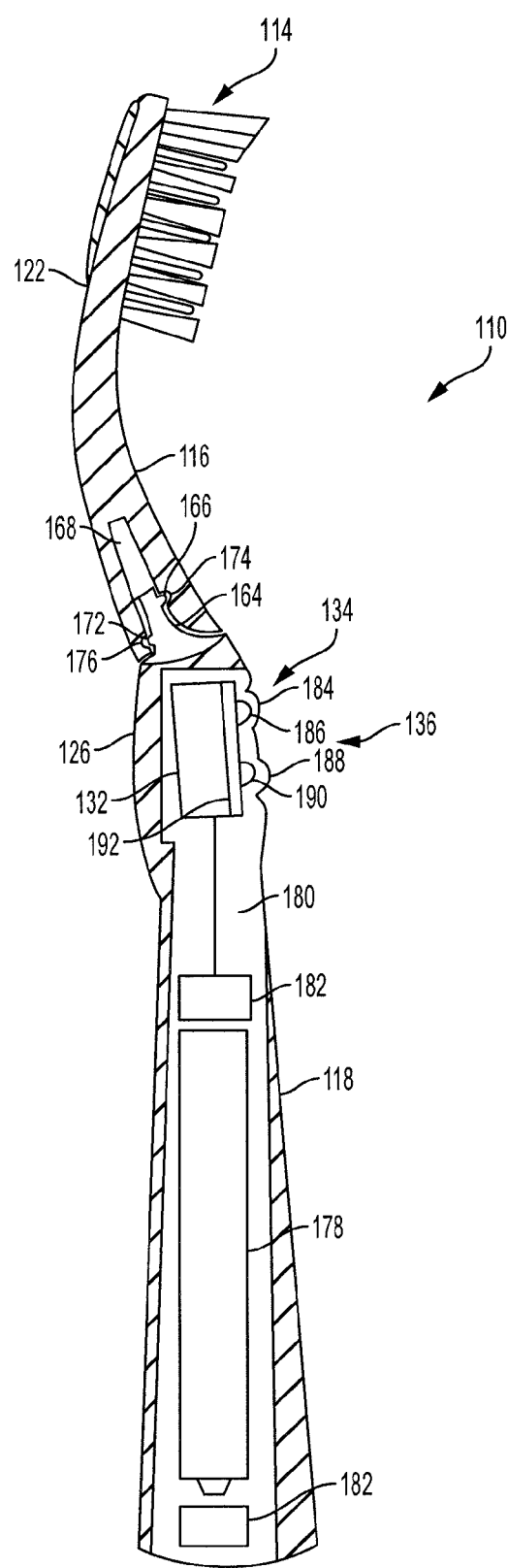
FIG. 20 is a cross sectional view of a toothbrush along line 20-20 in FIG. 16.

FIG. 20 illustrates a cross sectional view of the toothbrush 110 along line 20-20 in FIG. 16. The connector device 164 extends into the cavity 168. The respective catches 166, 172 may be configured to engage respective recesses 174, 176 in the interior surface of the neck portion 116. The catches 166, 172 may form a friction fit within the respective recesses 174, 176 to allow the neck portion 116 to separably couple to the handle portion 118.

A power source 178 may be positioned in an interior cavity 180 of the handle portion 118. The power source 178 may be in the form of at least one battery that is removable from the interior cavity 180. In one embodiment, the power source 178 may be a battery that is not removable from the interior cavity 180, or may be plug for inserting into a wall socket, or another form of power source. Power terminals 182 may couple to the power source 178 to transfer power from the power source 178 for powering the motor 132.

The power switch 134 may include a push button 184 and an electrical actuator 186. The push button 184 may form a flexible portion of the handle portion 118 to be pushed by a user. The electrical actuator 186 may be positioned in the interior cavity 180 of the handle portion 118 and may be configured to complete a circuit to either power or unpower the motor 132. The off switch 136 may include a push button 188 and an electrical actuator 190. The push button 188 may form a flexible portion of the handle portion 118 to be pushed by a user. The electrical actuator 190 may be positioned in the interior cavity 180 of the handle portion 118 and may be configured to complete a circuit to either power or unpower the motor 132. The electrical actuators 186, 190 may both be positioned on a circuit board 192. The circuit board 192 may include circuitry for controlling operation of the motor 132. In one embodiment, the circuit board 192 may include timer circuitry for automatically stopping operation of the motor 132 after a predetermined period of time elapses.

The neck portion 116 may have a curvature that is identical to the curvature of the neck portion 26. In one embodiment, the neck portion 116 may have a radius of curvature between about 3 and 4.5 centimeters. In one embodiment, the neck portion 116 may have a radius of curvature between about 3.5 and 4 centimeters. The neck portion 26 may include an identical radius of curvature as the neck portion 116. In one embodiment, the neck portion 116 may be supplied separate from the handle portion 118.

Any feature of toothbrush 110 may be incorporated into toothbrush 10 as desired.

The features of toothbrush 110 may beneficially allow the toothbrush to stand upright to increase usable counter space around a user's sink. The features of toothbrush 110 may also beneficially allow a user to readily interchange the neck portion and head portion with a different neck and head portion. Such a feature may allow a user to swap out the neck and head portion with a neck and head having different features, such as a different bristle profile, a different curvature of the neck, and other properties of the neck and head. The neck and head portion may also be easily replaced due to wear upon the neck and head, including wear upon the bristles. The structure of the connector device 164 may enhance the ease at which the neck and head portions may be replaced and secured to the handle portion. The use of the motor may beneficially enhance the brushing ability of the toothbrush 110.

Systems, methods and products are provided. References to "various embodiments", in "some embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

The foregoing description of the disclosed example embodiments is provided to enable any person of ordinary skill in the art to make or use the present invention. Various modifications to these examples will be readily apparent to those of ordinary skill in the art, and the principles disclosed herein may be applied to other examples without departing from the spirit or scope of the present invention. The described embodiments are to be considered in all respects only as illustrative and not restrictive and the scope of the invention is, therefore, indicated by the following claims rather than by the foregoing description. All changes which come within the meaning and range of equivalency of the claims are to be embraced within their scope.

What is claimed is:

1. A toothbrush comprising:
   a handle portion that extends along a midline axis and has a distal end and a proximal end;
   a head portion that does not contact or cross the midline axis and has a distal end and a proximal end, the distal end of the head portion and the proximal end of the handle portion having a linear distance and forming a linear axis;
   a plurality of bristles coupled to the head portion; and
   a curved neck portion having a proximal end coupled to the distal end of the handle portion at a juncture and a distal end coupled to the proximal end of the head portion, the curved neck portion and the head portion forming a continuous concave shape relative to the midline axis, and the curved neck portion being displaced from the linear axis by a displacement distance, the displacement distance being at least 6 percent of the linear distance from the proximal end of the handle portion to the distal end of the head portion, the curved neck portion configured to allow the head portion to access a rear portion of a user's mouth.

2. The toothbrush of claim 1, wherein the midline axis passes through the handle portion at the juncture and the handle portion extends along the midline axis at the juncture.

3. The toothbrush of claim 1, wherein the entirety of the handle portion extends upon the midline axis.

4. The toothbrush of claim 1, wherein the head portion is angled in a direction towards the midline axis.

5. The toothbrush of claim 1, wherein the plurality of bristles extend from the head portion in a direction towards the midline axis.

6. The toothbrush of claim 1, wherein the handle portion includes a base portion and a thumb grip portion, the juncture being at the thumb grip portion.

7. A toothbrush comprising:
a body having a proximal end, a distal end, a dorsal side, and a ventral side, the body including
  a handle portion that extends along a midline axis and has a distal end and a proximal end,
  a neck portion having a proximal end and a distal end, the neck portion being curved concave continuously relative to the dorsal side from the proximal end of the neck portion to the distal end of the neck portion, the distal end of the neck portion forming an angle with the midline axis of between eleven to eighteen degrees,
  a head portion having a distal end and a proximal end connected to the distal end of the neck portion, the head portion not contacting or crossing the midline axis, and
  a thumb grip portion coupled to the proximal end of the neck portion and the distal end of the handle portion; and
a plurality of bristles extending from the dorsal side of the body.

8. The toothbrush of claim 7, wherein the body has a linear distance from the proximal end of the body to the distal end of the body, and the neck portion has a linear distance parallel to the linear distance of the body that is at least about twenty five percent of the linear distance of the body.

9. The toothbrush of claim 7, wherein the thumb grip portion extends upon the midline axis.

10. The toothbrush of claim 9, wherein the head portion extends upon an axis that intersects the midline axis.

11. The toothbrush of claim 10, wherein the plurality of bristles are positioned on the head portion in a plurality of rows extending transverse to the axis the head portion extends upon.

12. The toothbrush of claim 11, wherein at least one of the plurality of rows includes bristle tufts angled towards a direction transverse to the axis the head portion extends upon.

13. A toothbrush comprising:
a body having a distal end, a proximal end, a linear distance from the distal end of the body to the proximal end of the body, and a linear axis for led by the distal end of the body and the proximal end of the body, the body including
  a handle portion being divided by a midplane into a dorsal side and a ventral side, with the dorsal side of the handle portion being positioned on a first side of the midplane and the ventral side of the handle portion being positioned on a second side of the midplane,
  a neck portion having a first end and a second end and a continuous curve that extends from the first end to the second end, the neck portion being coupled to the handle portion at the first end and having a displacement distance from the linear axis of the body being at least 6 percent of the linear distance of the body, and
  a head portion coupled to the second end of the neck portion and being angled towards the first side of the midplane as the head portion extends away from the second end of the neck portion, the head portion not contacting or crossing the midplane, the head portion and the neck portion forming a continuous concave shape relative to the midplane, the head portion configured to access a rear portion of a user's mouth via the neck portion; and
a plurality of bristles coupled to the head portion.

14. The toothbrush of claim 13, wherein the head portion is positioned entirely on the second side of the midplane.

15. The toothbrush of claim 13, wherein the plurality of bristles extend from the head portion in a direction away from the second side of the midplane.

16. The toothbrush of claim 13, wherein the handle portion includes a base portion and a thumb grip portion, the neck portion being coupled to the thumb grip portion.

17. The toothbrush of claim 13, wherein the handle portion extends upon an axis positioned on the midplane, the neck portion at the first end being angled away from the axis, the neck portion at the second end being angled towards the axis.

* * * * *